(12) United States Patent
Zhdanov

(10) Patent No.: US 7,550,969 B2
(45) Date of Patent: Jun. 23, 2009

(54) SECURITY SCREENING AND INSPECTION BASED ON BROADBAND ELECTROMAGNETIC HOLOGRAPHIC IMAGING

(75) Inventor: Michael S. Zhdanov, Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 1831 days.

(21) Appl. No.: 10/135,926

(22) Filed: Apr. 30, 2002

(65) Prior Publication Data

US 2009/0119040 A1    May 7, 2009

Related U.S. Application Data

(63) Continuation-in-part of application No. 09/876,262, filed on Jun. 6, 2001, now Pat. No. 6,876,878, which is a continuation-in-part of application No. 09/214,217, filed on Dec. 23, 1998, now Pat. No. 6,253,100.

(51) Int. Cl.
*G01R 33/12*      (2006.01)
*G01N 27/72*      (2006.01)

(52) U.S. Cl. .................................... 324/243; 324/232
(58) Field of Classification Search ............... 324/600, 324/243, 239, 228, 207.16, 207.22, 260, 324/207.17, 232
See application file for complete search history.

(56) References Cited

U.S. PATENT DOCUMENTS

| | | | |
|---|---|---|---|
| 3,887,923 A | 6/1975 | Hendriz |
| 3,953,822 A | 4/1976 | Vilkomerson |
| 4,755,944 A | 7/1988 | Glass |
| 4,852,575 A | 8/1989 | Nikoonahad |
| 4,945,239 A | 7/1990 | Wist et al. |
| 4,948,974 A | 8/1990 | Nelson et al. |
| 4,961,428 A | 10/1990 | Nikias et al. |
| 5,072,128 A | 12/1991 | Hayano et al. |
| 5,303,710 A | 4/1994 | Bashkansky et al. |
| 5,327,139 A | 7/1994 | Johnson |
| 5,363,050 A | 11/1994 | Guo et al. |
| 5,373,443 A | 12/1994 | Lee et al. |
| 5,413,098 A | 5/1995 | Benaron |
| 5,418,797 A | 5/1995 | Bashkansky et al. |

(Continued)

*Primary Examiner*—Long V Le
*Assistant Examiner*—Helene Bor
(74) *Attorney, Agent, or Firm*—McDermott Will & Emery LLP

(57) ABSTRACT

A method of security screening and inspection of people in airlines, ships, or secured buildings, involves placing an array of transmitters and receivers in operational association with the medium. The transmitters generate a broad band harmonic (frequency domain) or pulse (time domain) primary electromagnetic field (EM) field, including the lower frequency portions of the EM spectrum, whose propagation is typically characterized by the diffusion phenomena, or by the combination of the diffusion and wave phenomena. The primary field propagates through and interacts with the examined person and any objects carried by the person to produce a scattered field, which is recorded by the receivers. The scattered EM field components measured by the receivers are applied as an artificial EM field to generate a backscattering EM field. Cross power spectra of the primary and backscattering fields (in the frequency domain) or cross correlation between these fields (in the time domain) produce a numerical reconstruction of an EM hologram. The desired properties of the person, including the properties of any objects carried by the person, such as conductivity or dielectric permittivity, are then derived from this hologram.

44 Claims, 6 Drawing Sheets

U.S. PATENT DOCUMENTS

| | | |
|---|---|---|
| 5,435,312 A | 7/1995 | Spivey et al. |
| 5,476,108 A | 12/1995 | Dominguez et al. |
| 5,503,150 A | 4/1996 | Evans |
| 5,557,283 A * | 9/1996 | Sheen et al. ................ 342/179 |
| 5,588,032 A | 12/1996 | Johnson et al. |
| 5,592,170 A | 1/1997 | Price et al. |
| 5,606,969 A | 3/1997 | Butler et al. |
| 5,673,050 A | 9/1997 | Moussally et al. |
| 5,694,938 A | 12/1997 | Feng et al. |
| 5,715,819 A | 2/1998 | Svenson et al. |
| 5,807,257 A | 9/1998 | Bridges |
| 5,841,288 A | 11/1998 | Meaney et al. |
| 5,963,658 A | 10/1999 | Kilibanov et al. |
| 6,253,100 B1 | 6/2001 | Zhdanov |
| 6,507,309 B2 * | 1/2003 | McMakin et al. ............. 342/22 |
| 6,992,616 B2 * | 1/2006 | Grudkowski et al. ........ 342/179 |

* cited by examiner

SECURITY SCREENING AND INSPECTION BASED ON BROADBAND ELECTROMAGNETIC HOLOGRAPHIC IMAGING

This application is a continuation-in-part application of U.S. application Ser. No. 09/876,262, filed Jun. 6, 2001 now U.S. Pat. No. 6,876,878, which is a continuation-in-part application of U.S. application Ser. No. 09/214,217, filed Dec. 23, 1998 now U.S. Pat. No. 6,253,100, which claims priority from PCT application PCT/US97/11217, filed Jul. 26, 1997, which claims priority from U.S. Provisional Application 60/020,622, filed Jun. 26, 1996, entitled "METHOD OF BROAD BAND ELECTROMAGNETIC HOLOGRAPHIC IMAGING."

BACKGROUND OF THE INVENTION

1. Field of the Invention

This invention relates to three dimensional ("holographic") imaging. It is specifically directed to the electromagnetic (EM) imaging of an object within a non-transparent medium. It provides methodology and apparatus for conducting nondestructive and/or non-invasive inspections using broadband electromagnetic signals.

2. Description of the Related Art

Conventional optical holography constructs a volume (three dimensional) image of an object by displaying the amplitude and the phase structure of a wavefront of light. A reference wave of light is relied upon to facilitate the recording of both the amplitude and the phase condition of the object light by means of photographic emulsion. This reference wave is coherent with the object light and interferes with it, producing diffraction patterns, which form an optical hologram on the photographic emulsion. To generate a volume image, this optical hologram need merely be illuminated with a reference light wave. The resulting diffraction pattern wave (as scattered by the emulsion) is identical to the original wavefront of light scattered by the object, and therefore reproduces the volume image of the object.

U.S. Pat. No. 3,887,923 to Hendrix discloses an application of the principles of optical holography within the radio-frequency domain. The '923 patent discloses a passive radio direction finder which monitors the amplitude and phase of radio-frequency wave fronts across an aperture. An array of antennas sample the phase of incoming wave fronts. Each antenna is associated with a mixer, and one of the antennas provides a mixer reference signal for an input to each mixer. The signals are processed through an analog-to-digital converter and a computer programmed rapidly to execute Fourier transforms, eventually to produce a numerical reconstruction of the radio frequency hologram.

U.S. Pat. No. 5,299,033 to Leith, et al discloses a method whereby an image of an object embedded in a diffusing medium is formed by propagating a coherent light pulse through the diffusing medium and applying a reference pulse to gate precisely the first emerging light transmitted through the diffusing medium. To produce an image, it is necessary for the diffusing medium to be transparent, because the method relies upon optical light.

There have been several attempts to develop an imaging method, utilizing a low frequency electromagnetic (EM) field, especially as applied to the solution of geophysical problems. K. H. Lee and G. Xie, in both U.S. Pat. No. 5,373,443 and the article, "A new approach to imaging with low-frequency electromagnetic fields," Geophysics, volume 58, pages 780-796 (1993), describe a method for imaging electrical conductivity with low-frequency electromagnetic fields, using wavefield transforms and ray tomography. This work has recognized a relationship between low frequency diffusion EM field equations and wave equations, but practical applications of this method have been directed to defining interfaces, rather than three-dimensional imaging.

In the article entitled "Continuation of the transient electromagnetic field in the geoelectrical problems," Physics of the Earth (Izvestia Akademy Nauk—in Russian), No. 12, pages 60-69, 1981, the present inventor presented a mathematical transform, based upon the theory of Stratton-Chu integrals, of the field recorded on the earth's surface and scattered from a subsurface geological object downward to locate and image the object. Subsequently, the present inventor and M. A. Frenkel coauthored an article entitled "The solution of the inverse problems on the basis of the analytical continuation of the transient electromagnetic field in reverse time," J. Geomagn. Geolelectr., volume 35, pages 747-765 (1983), which developed this method and introduced an imaging concept based upon downward extrapolation of an EM field in reverse time (electromagnetic migration).

The inventor has further coauthored the articles: "Resistivity Imaging by Time Domain Electromagnetic Migration (TDEMM)" (with P. Traynin and O. Portniaguine), Exploration Geophysics, volume 26, pages 186-194 (1995), reporting work which tested the imaging concept using controlled-source electromagnetic data, with limited success for two-dimensional models only, and "Underground Imaging by Frequency Domain Electromagnetic Migration," (with P. Traynin and J. R. Booker), Geophysics, volume 61, No. 3, pages 666-682 (1996), explaining application of the migration method to natural EM field geophysical data interpretation, but this study was limited to two-dimensional magnetotelluric problems.

These earlier efforts to develop a method for quickly interpreting geophysical EM data over two-dimensional geoelectrical structures have met with limited success. Moreover, they have not pointed towards a practically useful method for accomplishing broadband EM imaging of three-dimensional objects in nontransparent media. There remains a need for a method of imaging capable of providing the volume image of objects located in nontransparent media similar to images produced by optical or radio-wave holography. Such a method would be useful in geophysical exploration, in environmental study (for example, in searching for buried mines), for nondestructive detection of defects in metal and in medical applications (for example, in breast cancer or diseased bone diagnoses).

SUMMARY OF THE INVENTION

In one embodiment, a system of security screening a body and attached object comprises a portal that includes at least one transmitter coil and at least one receiver coil. The portal is configured to accommodate and pass therethrough the body and an attached object. The transmitter coil generates a broadband electromagnetic field comprising a frequency domain and/or time domain electromagnetic field that propagates through and interacts with the body and attached object. This interaction results in a scattered electromagnetic field that is received and recorded by the receiver coil. A computer then: (a) simulates a first background electromagnetic field existing within the portal when no body or attached object is in the portal; (b) computes a first backscattering electromagnetic field obtainable by transmitting the scattered electromagnetic field from the receiver coil; (c) produces an image of electric conductivity and/or dielectric permittivity of the body and any attached object; and (d) determines at least one characteristic of the attached object.

In one aspect, the attached object comprises a weapon. In another aspect, the determined characteristic of the attached object is material composition. In another aspect, the determined characteristic of the attached object is shape.

In another aspect, the computer is configured to produce the image of electric conductivity and/or dielectric permittivity by calculating cross power spectra of the first background electromagnetic field and the first backscattering electromagnetic field. In another aspect, the computer is configured to produce the image of electric conductivity and/or dielectric permittivity by calculating cross correlation functions between the first background electromagnetic field and the first backscattering electromagnetic field.

In another aspect, the system of security screening a body and attached object further comprises one or more support posts connected to the portal, and configured to support the portal. In another aspect, the support posts are adjustable in height. In another aspect, the portal is adjustable in height along the support posts.

In another aspect, the computer is configured to produce the image of electric conductivity and/or dielectric permittivity iteratively by: (a) calculating a second background electromagnetic field in response to the first background electromagnetic field with a previously obtained complex conductivity; (b) calculating a residual electromagnetic field between the second background electromagnetic field and the first backscattering electromagnetic field; (c) calculating a second backscattering field for the residual electromagnetic field by simulating illumination of the updated background medium with electric and magnetic currents equivalent to those of the updated residual electromagnetic field recorded at the location of the receivers; and (d) constructing the updated volume images of anomalous conductivity $\sigma_{a(n)}(r)$ and of anomalous permittivity $\in_{a(n)}(r)$ on the basis of updated cross power spectrum or cross correlation functions between said first background field and said second backscattering field, using regularization procedures.

In another aspect, the system of security screening a body and attached object further comprises a converter configured to: (a) receive analog signals of the scattered electromagnetic field from the receiver coils; (b) convert the received analog signals into digital signals of the scattered electromagnetic field; and (c) transmit the scattered electromagnetic field to the computer.

In one embodiment, a method of security screening a body and attached object comprises providing a portal adapted to passably receive the body and attached object. The portal includes at least one transmitter coil and at least one receiver coil. The transmitter coil generates a broadband electromagnetic field comprising a frequency domain and/or time domain electromagnetic field that propagates through and interacts with the body and attached object. This interaction results in a scattered electromagnetic field that is received and recorded by the receiver coil. A first background electromagnetic field existing within the portal when no body or attached object is in the portal is simulated. A first backscattering electromagnetic field obtainable by transmitting the scattered electromagnetic field from the receiver coil is computed. An image of electric conductivity and/or dielectric permittivity of the body and any attached object is produced. At least one characteristic of the attached object is determined.

In another aspect, the step of producing the image of electric conductivity and/or dielectric permittivity further comprises calculating cross power spectra of the first background electromagnetic field and the first backscattering electromagnetic field. In another aspect, the step of producing the image of electric conductivity and/or dielectric permittivity further comprises calculating cross correlation functions between the first background electromagnetic field and the first backscattering electromagnetic field.

In another aspect, the method of security screening a body and attached object further comprises connecting one or more support posts to the portal, wherein the support posts are configured to support to portal.

In another aspect, the step of producing the image of electric conductivity and/or dielectric permittivity iteratively further comprises: (a) calculating a second background electromagnetic field in response to the first background electromagnetic field with a previously obtained complex conductivity; (b) calculating a residual electromagnetic field between the second background electromagnetic field and the first backscattering electromagnetic field; (c) calculating a second backscattering field for the residual electromagnetic field by simulating illumination of the updated background medium with electric and magnetic currents equivalent to those of the updated residual electromagnetic field recorded at the location of the receivers; and (d) constructing the updated volume images of anomalous conductivity $\sigma_{a(n)}(r)$ and of anomalous permittivity $\in_{a(n)}(r)$ on the basis of updated cross power spectrum or cross correlation functions between said first background field and said second backscattering field, using regularization procedures.

In another aspect, the method of security screening a body and attached object further comprises: (a) receiving analog signals of said scattered electromagnetic field from said receiver coils; and (b) converting said received analog signals into digital signals of said scattered electromagnetic field. In another aspect, the method of security screening a body and attached object further comprises: (a) recording said generated electromagnetic field with said received coils; and (b) filtering said generated electromagnetic field from said scattered electromagnetic field.

DETAILED DESCRIPTION OF THE PREFERRED EMBODIMENT

Figure 1:
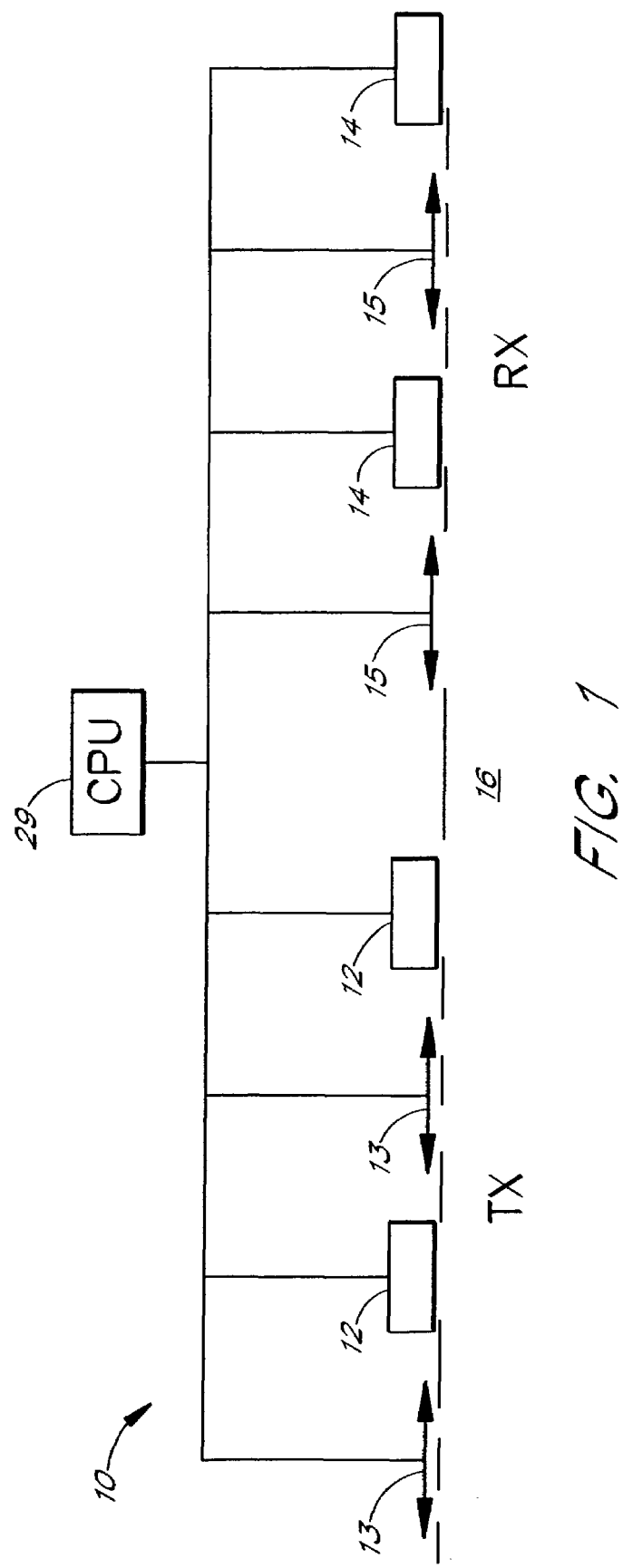
FIG. 1 illustrates an EM transmitting/receiving system placed on the surface of an examined medium.

A presently preferred approach to broad band EM holography is illustrated by FIG. 1. As illustrated, the imaging system 10 includes induction 12 or galvanic 13 EM field transmitters and induction 14 or galvanic 15 EM field receivers placed on the surface of the examined medium 16 (FIG. 1). The array of receivers 14, 15 may either be one-dimensional (as shown) or two-dimensional (typically, distributed in a grid pattern across the surface of observation). Transmitters 12, 13 (or a single transmitter) can be located arbitrarily on the surface of the examined medium 16.

Figure 3:
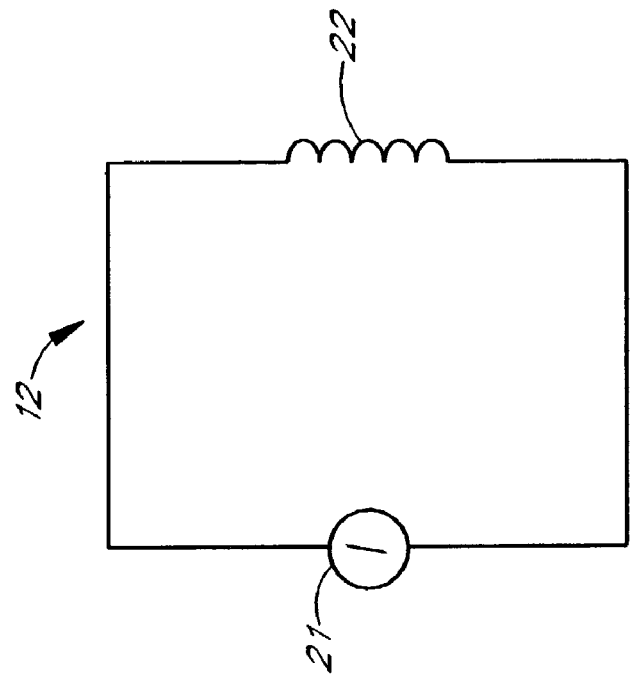
FIG. 3 is a simplified diagram of an induction transmitter useful in the system of FIG. 1.
Figure 2:
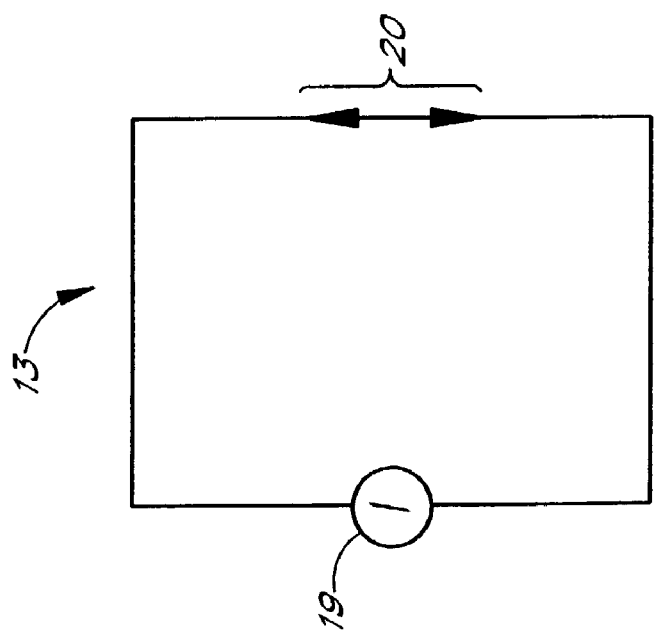
FIG. 2 is a simplified diagram of a galvanic transmitter useful in the system of FIG. 1.
Figure 5:
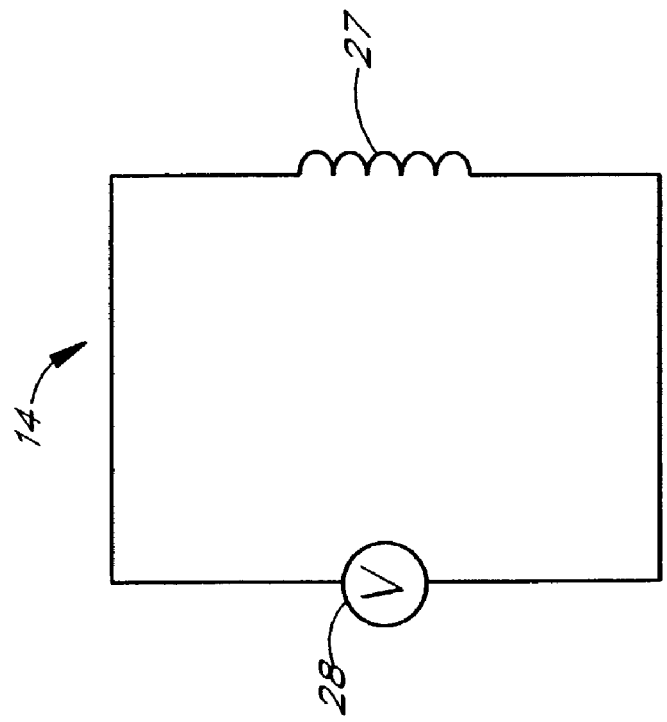
FIG. 5 is a simplified diagram of an induction receiver useful in the system of FIG. 1.
Figure 4:
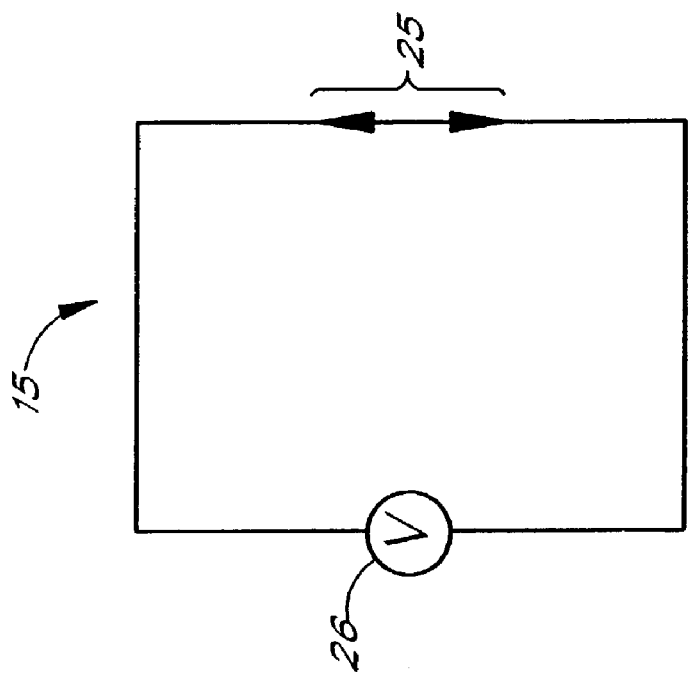
FIG. 4 is a simplified diagram of a galvanic receiver useful in the system of FIG. 1.

The galvanic transmitter 13 (FIG. 2) includes the transient current source 19 connected across the pair of current electrodes 20. The induction transmitter 12 (FIG. 3) includes the transient current source 21 connected across a solenoid coil 22. The galvanic receiver 15 (FIG. 4) includes a pair of receiver electrodes 25 connected across the voltmeter 26. The induction receiver 14 (FIG. 5) includes a solenoid coil 27 connected across the voltmeter 28. In use, galvanic devices are positioned in direct contact with the examined medium, but induction devices are operable from positions in the proximity of, but not necessarily in contact with, the examined medium.

Figure 6:
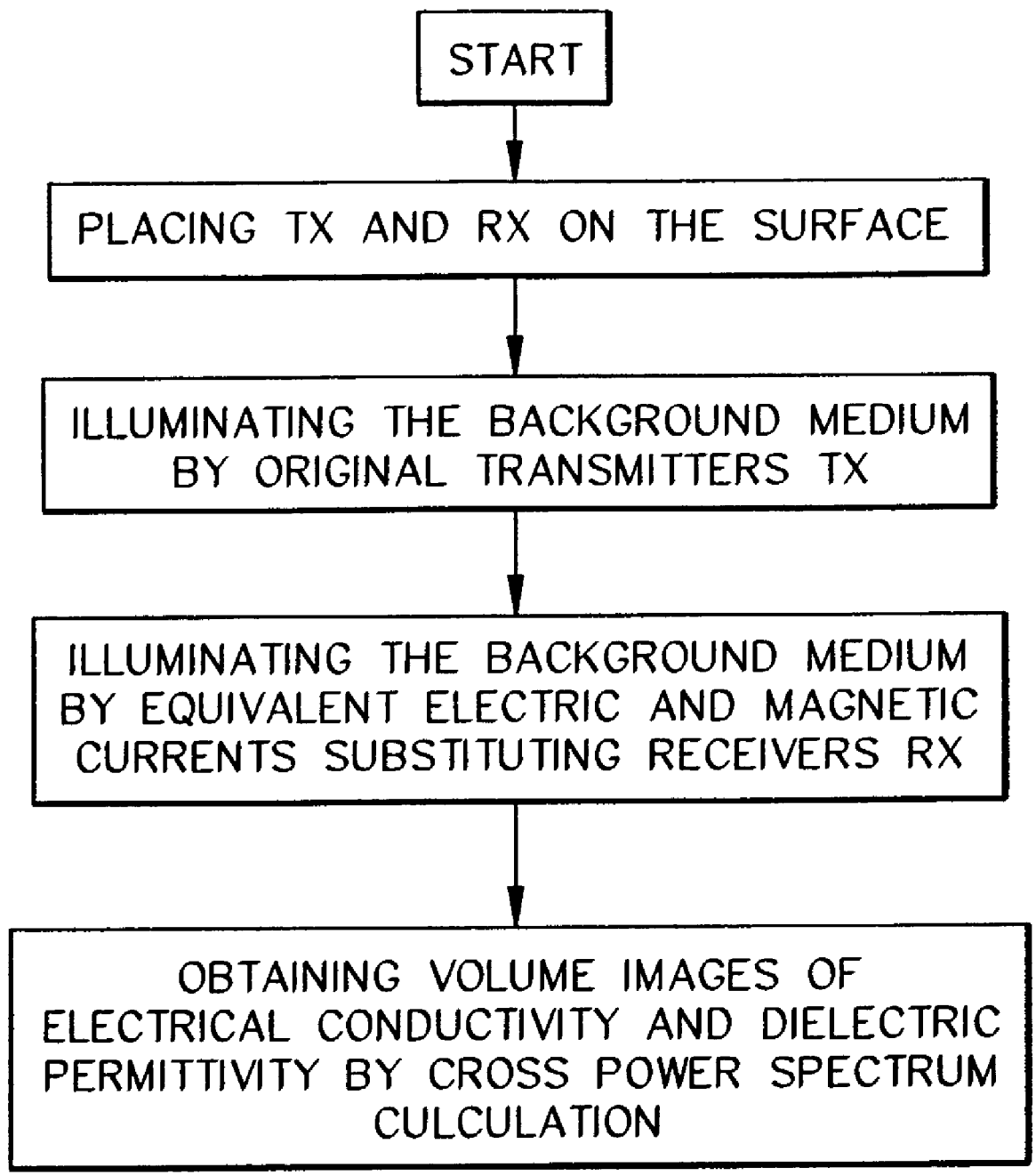
FIG. 6 is a flowchart illustrating a method of holographic imaging by the broad band EM system of FIG. 1.

The central processing unit 29 (FIG. 1) operates the broad band EM holographic imaging system, as it is schematically shown by FIG. 6. The incoming EM field generated by a transmitter (or, as illustrated, an array TX of transmitters) is received by an array of receivers RX, and is recorded by the central processing unit 29. In the output of the receiver array shown in FIG. 1, the EM field measurements are inherently reduced to numerical values. It is thus expedient to proceed with a numerical reconstruction of the volume image.

EXAMPLE 1

The following explanation of the principles of broad band EM holographic imaging reconstruction is offered to assist those skilled in the art to practice the invention. It is not intended thereby to limit the scope of the invention to any particular theory of operation or to any field of application.

A three dimensional inhomogeneous medium, with a known background complex conductivity, $\tilde{\sigma}_b$, contains a local inhomogeneous object D with an arbitrarily varying complex conductivity $\tilde{\sigma} = \tilde{\sigma}_b + \tilde{\sigma}_a$. The location of D and its anomalous conductivity $\tilde{\sigma}_a$, are unknown. The examined medium is considered to be non-magnetic, and hence $\mu = \mu_0 = 4\pi \times 10^{-7} H/m$, where $\mu$ is the magnetic permeability and $\mu_0$ is the free-space magnetic permeability. The model is excited by an EM field generated by a given system of sources (transmitters TX) with an electric current density $j^e$. This field is time harmonic as $e^{-i\omega t}$ and is observed by the system of receivers RX located on the surface S of the examined medium. Complex conductivity includes the effect of displacement currents: $\tilde{\sigma} = \sigma - i\omega \in$, where $\sigma$ and $\in$ are electrical conductivity and dielectric permittivity. The total EM field observed in this model can be represented as a sum of background (normal) field $\{E^b, H^b\}$ generated by the given system of transmitters in the model with the background conductivity distribution, and an anomalous field $\{E^a, H^a\}$, due to an inhomogeneity $\tilde{\sigma}_a(r)$:

$$E = E^b + E^a, H = H^b + H^a \quad (1)$$

where r is the radius vector of the observation point.

To generate the volume image of the object within the inhomogeneous medium, the same transmitter/receiver system is re-deployed in the same spatial configuration as used for the receiving mode of operation, on the surface of the medium with the conductivity equal to the background conductivity $\tilde{\sigma}_b$ (background medium). The receivers are operated as (or replaced by) auxiliary transmitters which generate electric $j_s^e$ and magnetic $j_s^m$ currents equivalents to those evaluated from the anomalous field previously recorded by the receivers, located on the surface S:

$$j_s^e = -n \times H^{a*},$$

$$j_s^m = n \times E^{a*}, \quad (2)$$

where n is the unit vector of normal to S pointing outward the examining medium, and * indicates a complex conjugate value.

A typical imaging process thus comprises:

1. Illuminating the background medium by a selected system of transmitters (background field $\{E^b, H^b\}$ generation).

2. Illuminating the background medium by artificial transmitters located in the positions of the receivers and operated in response to equivalent (fictitious) electric $j_s^e$ and magnetic $j_s^m$ currents, determined by formulae (2) (backscattering anomalous field $\{E^{as}, H^{as}\}$ generation).

3. Producing a broadband holographic image by calculating cross power spectra of the background and backscattering fields.

Referring to FIGS. 1 and 6, the operation of imaging system 10 can be summarized as follows: An electromagnetic signal is generated by transmitters 12, 13, and is recorded by receivers 14, 15, placed on the surface of an examined medium, (for example, the earth or the body of a human being). The CPU system 29 analyzes the recorded field and fulfills the following numerical processes:

(1) It numerically stimulates illumination of the background medium by the original system of transmitters TX.

(2) It computes the backscattering anomalous field $\{E^{as}, H^{as}\}$, simulating illumination of the background medium by equivalent electric and magnetic currents, substituting the receivers RX.

(3) It constructs the volume images of electrical conductivity and dielectric permittivity by calculating cross power spectra of the background and backscattering fields.

EXAMPLE 2

The image generating method solves the minimum energy flow problem for the residual field $\{E^\Delta, H^\Delta\}$ computed as the difference between the observed field $\{E_{obs}, H_{obs}\}$ and numerically calculated (predicted) field $\{E_{pr}, H_{pr}\}$ for a constructed image.

The energy flow of the residual electromagnetic field can be calculated using the complex Poynting vector P, introduced by the formula:

$$P = \frac{1}{2} E^\Delta \times H^{\Delta*}, \quad (3)$$

which is known to be a non-negative function.

The measure $\Phi$ of the difference between the observed and predicted fields can be introduced as the energy flow of the residual field through the surfaces of observations, integrated over the frequency $\omega$:

The theoretical predicted fields $E_{pr}(r, \omega)$, $H_{pr}(r, \omega)$ depend on the sum of the background $\tilde{\sigma}_b(r)$ and anomalous conductivity distribution $\tilde{\sigma}_a(r)$ in the examined $$\Phi = \text{Re} \int_\Omega \int \int_S P \cdot n \, ds \, d\omega = \quad (4)$$

$$\frac{1}{2} \text{Re} \int_\Omega \int \int_S [E^\Delta(r, \omega) \times H^{\Delta^*}(r, \omega)] \cdot n \, ds \, d\omega$$

medium, and, therefore, the residual field energy flow φ is a function of $[\tilde{\sigma}_b(r)+\tilde{\sigma}_a(r)]$:

$$\phi = \phi[\tilde{\sigma}_b + \tilde{\sigma}_a]. \quad (5)$$

It can be expressed approximately as:

$$\phi[\tilde{\sigma}_b + \tilde{\sigma}_a] \approx \phi(\tilde{\sigma}_b) + \delta\phi(\tilde{\sigma}_b, \tilde{\sigma}_a) \quad (6)$$

where $\delta\phi(\tilde{\sigma}_b, \tilde{\sigma}_a)$ is a gradient of the residual field energy flow. It is a linear function of anomalous conductivity and is computed by the formula:

$$\delta\phi(\tilde{\sigma}_b, \tilde{\sigma}_a) = \quad (7)$$
$$-\frac{1}{2}\text{Re} \int \int \int_D \int_\Omega \tilde{\sigma}_a(r') \int \int_S n \cdot \left\{ E^{a^*}(r,\omega) \times \hat{G}_H^b(r\,|\,r',\omega) - H^{a^*}(r,\omega) \times \hat{G}_E^b(r\,|\,r',\omega) \right\} ds \cdot E^b(r',\omega) d\omega dv',$$

where v is the volume and dv is the elemental volume of integration and where $\hat{G}_E^b$ and $\hat{G}_H^b$ are electric and magnetic Green's tensors for the background conductivity $\tilde{\sigma}_b(r)$, whose vector components relate the electric and magnetic fields excited at the point r by an electric dipole source of unit intensity located at the point r' of the domain D.

It is known from the literature that the integral over the surface of observation can be treated as the backscattering anomalous electric field $E^{as}(r',\omega)$:

$$E^{as}(r',\omega) = \int \int_S \{j_S^m(r,\omega) \cdot \hat{G}_H^b(r|r',\omega) + j_S^e(r,\omega) \cdot \hat{G}_E^b(r|r',\omega)\} ds = \int \int_S n \cdot \{E^{a*}(r,\omega) \times \hat{G}_H^b(r|r',\omega) - H^{a*}(r,\omega) \times \hat{G}_E^b(r|r',\omega)\} ds. \quad (8)$$

Therefore, in accordance with the equations (7) and (8) and the formula $\tilde{\sigma}_a(r') = \sigma_a(r') - i\omega\epsilon_a(r')$, the gradient of the residual field energy flow becomes:

$$\delta\phi(\tilde{\sigma}_b, \tilde{\sigma}_a) = \quad (9)$$
$$-\frac{1}{2}\text{Re} \int \int \int_D \int_\Omega [\sigma_a(r') - i\omega\epsilon_a(r')] E^b(r',\omega) \cdot E^{as}(r',\omega) d\omega dv' =$$
$$-\frac{1}{2} \int \int \int_D \sigma_a(r') A(r') dv' - \frac{1}{2} \int \int \int_D \epsilon_a(r') B(r') dv',$$

where A(r) is a cross power spectrum of background and backscattering fields, computed by the formula:

$$A(r) \approx \text{Re} \int_\Omega E^b(r,\omega) \cdot E^{as}(r,\omega) d\omega, \quad (10)$$

B(r) is a cross power spectrum of the time derivative of the background field and backscattering fields, computed by the formula:

$$B(r) \approx \text{Re} \int_\Omega (-i\omega) E^b(r,\omega) \cdot E^{as}(r,\omega) d\omega, \quad (11)$$

and Ω is the frequency range.

Equation (9) provides a choice of selecting $\tilde{\sigma}_a(r')$ minimizing φ:

$$\tilde{\sigma}_a(r') = \sigma_a(r') - i\omega\epsilon_a(r') = kA(r') - i\omega kB(r'), \quad (12)$$

taking into account, that:

$$\phi(\tilde{\sigma}_b + \tilde{\sigma}_a) = \quad (13)$$
$$\phi(\tilde{\sigma}_b + kA - i\omega kB) \approx \phi(\tilde{\sigma}_b(r)) + k\delta\phi(\tilde{\sigma}_b, A - i\omega B) = \phi(\tilde{\sigma}_b) -$$
$$\frac{1}{2} k \int \int \int_D |A(r')|^2 \, dv' - \frac{1}{2} k \int \int \int_D |B(r')|^2 \, dv' < \phi(\tilde{\sigma}_b),$$

where k>0 is a scale factor determined numerically by a linear search for the minimum of the functional:

$$\phi(\tilde{\sigma}_b + \tilde{\sigma}_a) = \phi(\tilde{\sigma}_b + kA - i\omega kB) = \phi(k) = \min. \quad (14)$$

Hence, one of the important features is the ability to produce anomalous electrical conductivity and dielectric permittivity of the target, which minimize the residual field energy flow through the receivers. Generally, this approach is referred to as the inverse problem solution, because the residual field is the difference between the observed data and numerically predicted data, and the goal is to determine the parameters (material properties and location) of the target. The present method resolves this inverse problem in a new way by minimizing the residual field flow. It is realized numerically through the following three steps:

Step 1. Calculating the background field $\{E^b, H^b\}$ by numerically solving the equations:

$$\nabla \times H^b = \sigma_b E^b + j^e,$$
$$\nabla \times E^b = i\omega\mu H^b, \quad (15)$$

assuming that the sources $j^e$ and background conductivity $\sigma_b$ are known. The numerical methods of solving this problem are well developed. (See Zhdanov M. S. and G. V. Keller "The geoelectrical methods in geophysical exploration," Elsevier, 1994). The calculations are simplified in the case of homogenous or one dimensional background conductivity $\sigma_b$.

Step 2. Calculating the backscattering anomalous field $\{E^{as}, H^{as}\}$, by numerically solving the equations:

$$\nabla \times H^{as} = \sigma_b E^{as} + j_S^e,$$
$$\nabla \times E^{as} = i\omega\mu H^{as} - j_S^m, \quad (16)$$

assuming that the sources $j_S^e$ and $j_S^m$ and background conductivity $\sigma_b$ are known. In particular, equation (16) can be solved using integral formula (8), which actually solves the boundary value problem for backscattering an anomalous field. The numerical methods of calculating electric and magnetic Green's tensors $\hat{G}_E^b$ and $\hat{G}_H^b$ for one dimensional background conductivity $\sigma_b(r)$ are also well developed. (See Zhdanov, M. S., Integral transforms in geophysics, Springer-Verlag, 1988.) In particular, for homogenous background conductivity, the Green's tensors can be determined by the formulae:

$$\hat{G}_E^b = \left(\hat{I} + \frac{1}{i\omega\mu\tilde{\sigma}_b}\nabla\nabla\right)G^b, \quad \hat{G}_E^b = \frac{1}{i\omega\mu}\nabla \times \hat{I}G^b, \quad (17)$$

where $\hat{1}$ is a unit tensor and $G^b$ is a scalar Green's function for the Helmholtz equation, calculating by the expression:

$$G^b = G^b(r \mid r', \omega) = -\frac{\exp\left[-(1-i)\sqrt{\omega\mu\tilde{\sigma}_b/2}\,|r-r'|\right]}{4\pi|r-r'|}. \quad (18)$$

Numerical algorithm for backscattering anomalous field reconstruction is given by the formula deriving from equation (8):

$$E_{as}(r',\omega) = \sum_{j=1}^{N} n(r_j) \cdot \{E^{a*}(r_j,\omega) \times \hat{G}_H^b(r_j|r',\omega) - H_a^*(r_j,\omega) \times \hat{G}_E^b(r_j|r',\omega)\}\Delta S_j. \quad (19)$$

In the case when transmitters generating a pulse (time domain) background EM field which propagates through the medium containing the object, the calculation of the backscattering field in time domain can be fulfilled by the formula (see Zhdanov, M. S., Integral transforms in geophysics, Springer-Verlag, 1988):

$$E^{as}(r',-t') = \int_T \int\int_S n \cdot \{E^a(r,t) \times \hat{G}_H^b(r,t|r',t') - H^a(r,t) \times \hat{G}_E^b(r,t|r',t')\}ds dt. \quad (20)$$

The corresponding numerical formula in time domain has the form:

$$E^{as}(r',-t') = \sum_{l=1}^{L}\sum_{j=1}^{N} n(r_j) \cdot \{E^a(r_j,t_l) \times \hat{G}_H^b(r_j,t_l|r',t') - H^a(r_j,t_l) \times \hat{G}_E^b(r_j,t_l|r',t')\}\Delta S_j \Delta t_l. \quad (21)$$

Step 3. Constructing the volume images of anomalous conductivity $\sigma_a$ and of anomalous permittivity $\in_a$ distributions (the broad band EM holographic images) by calculating cross power spectrum $A(r)$ of background and backscattering fields and cross power spectrum $B(r)$ of the time derivative of the background field and backscattering field:

$$\sigma_a(r) \approx kA(r) = kRe\sum_{m=1}^{M} E^b(r,\omega_m) \cdot E^{as}(r,\omega_m)\Delta\omega_m,$$

$$\in_a = kB(r) = kRe\sum_{m=1}^{M}(-i\omega_m)E^b(r,\omega_m) \cdot E^{as}(r,\omega_m)\Delta\omega_m. \quad (22)$$

In time domain the calculation of cross power spectrums $A(r)$ and $B(r)$ can be reduced to cross correlation between the background and backscattering anomalous fields and between time derivative of the background field and backscattering field:

$$A(r) \approx \int_T E^b(r,t) \cdot E^{as}(r,-t)dt, \quad (23)$$

$$B(r) \approx \int_T \frac{\partial E^b(r,t)}{\partial t} \cdot E^{as}(r,-t)dt.$$

where T is time interval. The last formulae can be computed numerically by the following expressions:

$$A(r) \approx \sum_{l=1}^{L} E^b(r,t_l) \cdot E^{as}(r,-t_l)\Delta t_l, \quad (24)$$

$$B(r) \approx \sum_{l=1}^{L} \frac{\partial E^b}{\partial t}(r,t_l) \cdot E^{as}(r,-t_l)\Delta t_l.$$

The volume images of anomalous conductivity $\sigma_a(r)$ and of anomalous permittivity $\in_a(r)$ are constructed on the basis of cross power spectra $A(r)$ and $B(r)$ by formula (12).

EXAMPLE 3

It is possible to improve the resolution of imaging by repeating the steps of the previous examples iteratively. This procedure solves the inverse problem for determination of the material properties and location of the target.

The general iterative process can be described by the formula:

$$\sigma_{a(n+1)}(r) = \sigma_{a(n)}(r) + k_n A_n(r) - i\omega B_n(r) \quad (25)$$

where n=1, 2, 3, . . . , N; $k_1$=k; $A_1(r)$=A(r), $B_1(r)$=B(r); and $\tilde{\sigma}_{a(1)}(r) = \sigma_a(r) - i\omega kB(r) = kA(r) - \omega kB(r)$.

The cross power spectra on the n-th iteration $A_n(r)$ an $dB_n(r)$ can be calculated by formulae, analogous to (1) and (11) in the frequency domain:

$$A_n(r) = Re\int_\Omega E_n^b(r,\omega) \cdot E_n^a(r,\omega)d\omega,$$

$$B_n(r) = Re\int_\Omega (-i\omega) E_n^b(r,\omega) \cdot E_n^b(r,\omega)d\omega, \quad (26)$$

where $E_n^b(r,\omega)$ is the corrected background field calculated by forward modeling for the geoelectrical model with the corrected background conductivity distribution $\sigma_{b(n)} = \tilde{\sigma}_{a(n)} + \sigma_{a(n)}$, and $E_n^a(r,\omega)$, is the corrected backscattering field of the corrected residual field $E^{\Delta n}$, which is the difference between the observed field and the corrected background field $E_n^b(r,\omega)$, found on the n-th iteration.

In the time domain, the functions $A_n(r)$ and $B_n(r)$ on the n-th iteration are determined by the cross correlation between corrected background and corrected backscattering fields according to the formulae:

$$A_n(r) = \int_T E_n^b(r,t) \cdot E_n^a(r,-t)dt \quad (27)$$

$$B_n(r) = \int_T \frac{\partial E_n^b(r,t)}{\partial t} \cdot E_n^{as}(r,-t)dt.$$

On every iteration, the same steps are applied:

Step 1. Calculating an updated (corrected) background field as electromagnetic response for the updated background medium with the complex conductivity $\sigma_{b(n)}(r)$, obtained on the previous iteration.

Step 2. Calculating the updated residual field between this response and observed field, and then calculating the updated backscattering field for the updated residual field by simulating illumination of the updated background medium with electric and magnetic currents equivalent to those of the updated residual field recorded at the location of the receivers.

Step 3. Constructing the updated volume images of anomalous conductivity $\sigma_{a(n)}(r)$ and of anomalous permittivity $\in_{a(n)}(r)$ on the basis of updated [according to the formulae (26) and (27)] cross power spectra $A_n(r)$ and $B_n(r)$ $$\sigma_{a(n)}(r) = k_n A_n(r), \in_{a(n)}(r) = k_n B_n(r) \quad (28)$$

where $k_n$>0 is a scale factor calculated using the line each for minimum of the energy functional:

$$\Phi(\sigma_b + \sigma_{a(n+1)}) = \Phi(\sigma_b + \sigma_{a(n)} + k_n A_n - i\omega k_n B_n) = \min. \quad (29)$$

The iterations can be terminated when the functional $\Phi(\sigma_b + \sigma_{a(n+1)})$ reaches the required accuracy level.

Thus, the computer of the system may be operated iteratively through the steps of: (1) updating the background field obtained in a previous iteration by adding the volume image constructed during that previous iteration; (2) repeating at least the steps of the method involving measuring (either empirically or numerically) the scattered electromagnetic field with the receivers through obtaining a next generation iteration of a volume image; and (3) repeating steps (1) and (2) until the updated background medium approximates the updated volume image. Regularization procedures such as described in M. S. Zhdanov and G. Hursan, 2000, 3-D electromagnetic inversion based on quasi-analytical approximation, Inverse Problems, 16, 1297-1322 can be used in the iterative process to generate a stable and resolved image.

Reference in this disclosure to details of specific embodiments is not intended to limit the scope of the appended claims.

INDUSTRIAL APPLICABILITY

The method can be applied in a variety of contexts. For example, internal defects in metal or concrete constructions can be located and imaged. The method is also useful for locating and imaging underground geological structures in connection with exploration for mineral, hydrocarbons and groundwater and in connection with environmental clean up activities. A particularly promising application involves imaging internal structures of living animals, notably the internal organs of the human body. To examine a diseased liver, for example, a normal body may serve as a reference model from which to derive a background field. To examine a diseased bone, such as in the case of osteoporosis, a normal bone may serve as a reference model.

Application for Breast Cancer, Osteoporosis, and Other Diseases Screening

Studies have shown that diseased human body parts often possess an abnormal level of conductivity and/or dielectric permittivity. For example, Colton and Monk (1995) reported that the presence of leukemia in bone marrow causes an increase in the dielectric permittivity and a decrease in the conductivity of the marrow. By determining the electrical conductivity and dielectric permittivity of a patient's tissues, broad band electromagnetic imaging methods can be used to detect diseased tissues, such as malignant tumor, and to differentiate diseased tissues from normal tissues.

Broad band electromagnetic imaging methods have many advantages over traditional examination methods such as X-ray. For example, broadband electromagnetic imaging methods are safer because they use electromagnetic energy that is non-ionizing. Broadband electromagnetic imaging methods are also safer because they use low-frequency energy typically in the 1-100 MHz range, lower than X-ray energy that is typically in the 1 GHz range. Broadband electromagnetic imaging methods are also patient-friendly, because they do not necessarily require contact with a patient's body or compression of a patient's body.

One of the uses of broadband electromagnetic imaging methods in the medical field is breast cancer screening. By measuring the conductivity and dielectric permittivity of a patient's breasts, malignant tissue whose conductivity and/or dielectric permittivity are different from normal tissue can be detected. Broadband electromagnetic imaging methods can also be used in combination with other screening methods such as palpation or mammography to increase cancer-detection rate and to reduce false-positive rate.

In addition to breast cancer screening, broadband electromagnetic imaging methods can also be used to examine other body parts for other diseases, including animal body parts for diseases. For example, broadband electromagnetic imaging methods can be used for osteoporosis screening, to detect abnormal bones with density loss. By producing a 3-D image of conductivity and permittivity of bones, the described methods can detect abnormal bones and provide valuable information to medical doctors and patients. The frequency of the electromagnetic energy used in the examination may be adjusted to allow desired penetration and contrast sensitivity of the body part examined. As described in Appendix A, which is incorporated by reference in its entirety, the frequency may be adjusted based on desired examination depth and density.

Application for Nondestructive Testing

Broadband electromagnetic imaging methods can also be used for nondestructive testing of technical structures. Technical structures such as walls, internal structural supports of buildings, aircraft structures and automobile structures are traditionally tested using eddy current testing, ultrasound testing, and other methods. Broadband electromagnetic imaging methods can be used to produce a 3-D image of conductivity and permittivity distribution within the examined structure. Compared to eddy current testing, which can only examine conductive structures, broadband electromagnetic methods can also examine non-conductive structures. Broadband electromagnetic methods also provide more detailed quantitative information on conductivity and permittivity distribution within the examined structure.

Application for Security Screening and Inspection

Broadband electromagnetic imaging methods can also be used for security screening and inspection of passengers of airlines and ships, as well as of visitors to offices and secured buildings. Security screening of passengers in airports is presently conducted using simple induction devices that respond to the presence of metal objects. Security inspection of luggage is conducted using X-rays. It is impractical to use the same X-ray screening machines for inspection of passengers because these X-ray machines use harmful radiation, which cannot be applied to passengers often. In contrast, broadband electromagnetic imaging methods can be used to produce a two dimensional or three dimensional image of any object carried by a passenger or attached to a passenger's body. Broadband electromagnetic imaging methods have many advantages over traditional examination methods such as X-ray. For example, broadband electromagnetic imaging methods are harmless to the passenger because they use low energy electromagnetic radiation that is non-ionizing. Therefore, they can be applied to passengers as often as necessary without any medical side effects. Compared to traditional induction devices, or to other radar-like hidden weapon detectors which can only detect the presence of the metal objects, broadband electromagnetic methods also provide detailed quantitative information on the structure of any object carried by a passenger.

Embodiments of a Medical Test Device

One embodiment of a test device includes a galvanic transmitter and a galvanic receiver. The galvanic transmitter includes a pair of current electrodes that are connected to the examined medium. A current of electricity is sent from the current electrodes to the examined medium. The galvanic receiver also includes a pair of current electrodes that are connected to the examined medium. The galvanic receiver measures the electric potential difference between its two current electrodes connected to the examined medium.

Another embodiment of a test device includes an inductive transmitter and an inductive receiver. The transmitter includes a solenoid induction coil. When electricity is sent to the coil, it induces a transient electromagnetic field that penetrates through the examined medium. The receiver also includes an induction coil. The receiver coil measures the electromagnetic field caused by electromagnetic response from the examined medium. The analog signals measured by the receiver are converted by a support electronics module into digital signals. One embodiment of a support electronics module is an analog-to-digital converter. The converted digital signals are then used by a computer to produce images of conductivity and/or dielectric permittivity. Compared to galvanic transmitters and receivers, inductive transmitters and receivers have the advantage of not requiring physical contact with the examined medium.

Figure 7A:
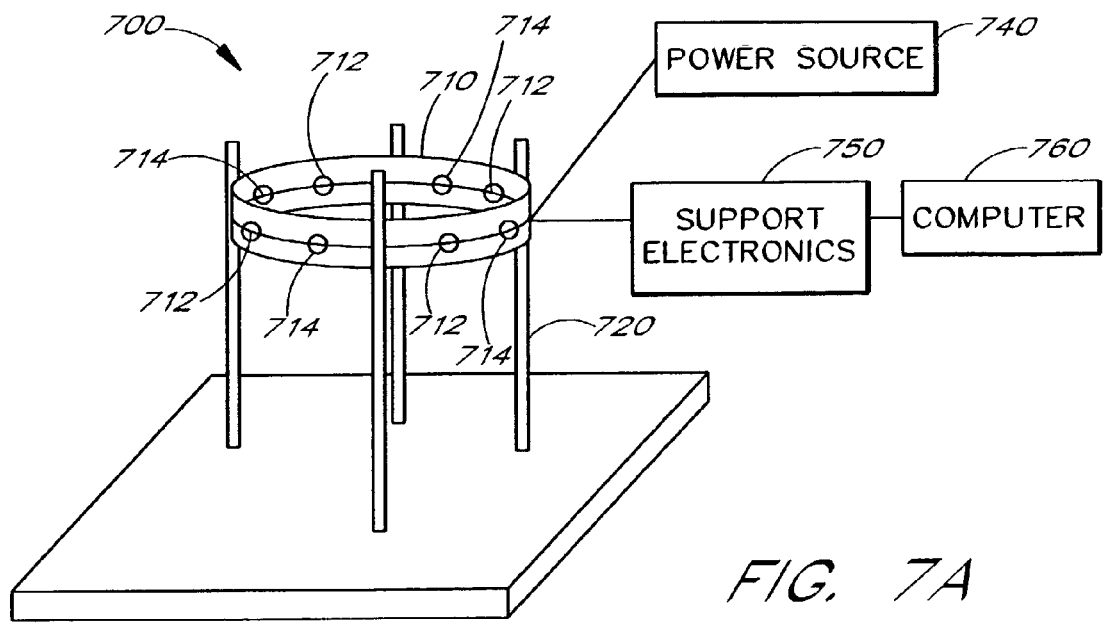
FIG. 7A is a diagram illustrating one embodiment of a medical test device.
Figure 7B:
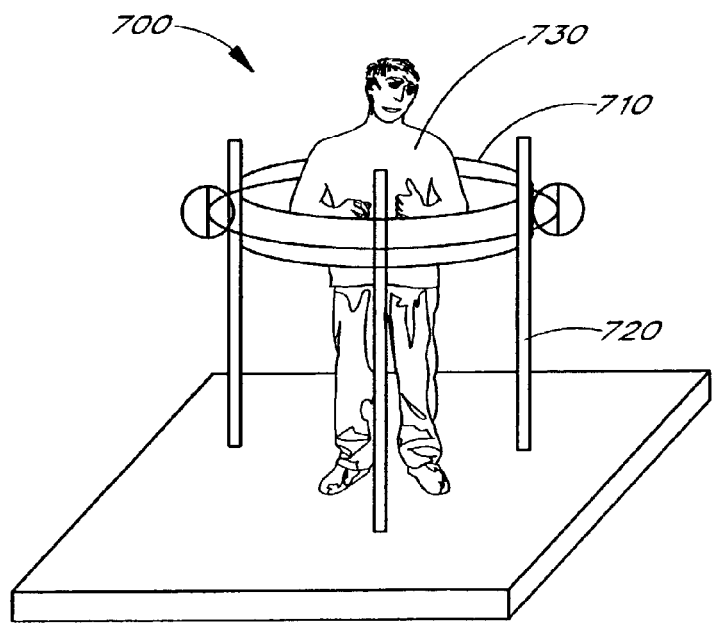
FIG. 7B is a diagram illustrating one embodiment of the medical test device as applied to a patient.

FIG. 7A and FIG. 7B illustrate one embodiment of a test device 700. As shown in FIG. 7A, one or more transmitter coils 712 and one or more receiver coils 714 are placed along a ring 710. The ring 710 is placed horizontally and supported by vertical posts 720. In one implementation illustrated in FIG. 7B, the ring 710 has a diameter (such as 1-2 meters) sufficient for a patient 730 to stand in. In another implementation, the ring 710 has a diameter (such as 10-20 centimeters) sufficient for a patient to insert a body part such as a hand, a foot, or a breast into the ring 710. In one implementation, the ring 710 can be moved up and down along the vertical posts 720, so that the ring 710 can be placed to examine multiple cross sections of the patient's body 730. For example, the ring 710 can be slidingly connected to the vertical posts 720, or connected to the vertical posts 720 using holes and clamps, so that the height of the ring 710 can be adjusted. In another implementation, the vertical posts 720 are adjustable in height (for example made of telescoping tubes), therefore making the ring 710 adjustable in height.

Referring back to FIG. 7A, the transmitter coils 712 are connected through the ring 710 to a power source 740. The receiver coils 714 are connected through the ring 710 to a support electronics module 750, which is connected to a computer 760. In one embodiment illustrated in FIG. 7A, four transmitter coils 712 and four receiver coils 714 are distributed along the ring 710. In another embodiment, eight transmitter coils 712 and sixteen receiver coils 714 are distributed along the ring 710.

During operation, electricity is sent from the power source 740 to the transmitter coils 712. The transmitter coils 712 illuminate the examined medium with electromagnetic field, to be recorded by the receiver coils 714. In one embodiment, the intensity of the signals has an approximate dynamic range between 100 dB to 140 dB (decibel). In one embodiment, the signal frequency is between approximately 1 megahertz and approximately 10 megahertz. In another embodiment, the signal frequency is between approximately 1 megahertz and approximately 100 megahertz. The electromagnetic signals generated by the transmitter coils 712 are called primary signals. The primary signals interact with the examined target inside the ring 710 and result in a scattered electromagnetic field of secondary signals. The receiver coils 714 record the primary signals and secondary signals and send the recorded signals to the support electronics module 750 for processing. The support electronics module 750 converts the received analog signals into digital signals, and filters out the primary signals. The remaining secondary digital signals are processed by the computer 760 to produce images of conductivity and/or dielectric permittivity of the examined area. In one implementation, the ring 710 is moved up and down the vertical posts 720, an examination is performed for every ring location on the vertical posts 720, in order to generate a plurality of cross sections of conductivity and dielectric permittivity data for the patient body 730.

In one embodiment, each of the coils can serve as both a transmitter coil and a receiver coil. For example, the coil 712 first serves as a transmitter, receives electricity from the power source 740 and illuminates the examined medium with electromagnetic field. Since electromagnetic field can at least partially remain for a short period of time, the coil 712 can then serve as a receiver and record the electromagnetic field.

Another embodiment of a test device (not shown) is a hand held device that includes a transmitter and a receiver. The hand held device is placed on or in proximity to a part of a patient body. The hand held device is connected to a support electronics module, which is connected to a computer. After conductivity and/or permittivity data of the part of the patient body is obtained, the hand held device can be placed on or in proximity to another part of the patient body. By moving the hand held device along a patient body surface, maps of conductivity and/or permittivity can be obtained.

Yet another embodiment of a test device (not shown) is a scanning chamber in a form similar to a MRI scan chamber. A patient is placed inside the chamber. One of more transmitters and one or more receivers placed on the interior wall of the chamber then respectively produce and record electromagnetic fields. The recorded analog signals are converted by a support electronics module to digital signals. The digital signals are then processed by a computer to produce images of conductivity and/or permittivity.

Still another embodiment of a test device (not shown) is a scanning bed with one or more adjustable straps. One or more transmitters and one or more receivers are placed on each of the straps. After a patient is placed on the bed, the straps are placed on the part of the patient body that is to be examined. Transmitters and receivers then respectively produce and record electromagnetic signals. In one embodiment, the straps can be removed from the bed and reattached to the bed, to be placed on another part of the patient body.

Each embodiment of the test device is connected to a support electronics module, which is connected by wire or wirelessly to a computer. After the receivers record a scattered electromagnetic field, the analog signals of the field is converted by the support electronics module to digital signals. The computer receives the digital signals of the scattered electromagnetic field from the support electronics module, creates a simulated homogeneous background field that represents the examined background medium (such as the patient's body) without the examined target (such as the patient's breast, liver, bone, etc.), creates a simulated backscattering anomalous field that represents an electromagnetic field obtainable by transmitting the scattered electromagnetic field from the receivers to illuminate the background medium, and produces a volume image of the conductivity and/or dielectric permittivity of the examined target. In one embodiment, the computer produces the volume image by calculating cross power spectra of the background field and the backscattering field. In another embodiment, the computer produces the volume image by calculating cross correlation functions between the background field and the backscattering field.

In yet another embodiment, the computer produces the volume image iteratively by:

Calculating an updated (corrected) background field as electromagnetic response for the updated background medium with the complex conductivity, obtained on the previous iteration;

Calculating the updated residual field between this response and observed field, and calculating the updated backscattering field for the updated residual field by simulating illumination of the updated background medium with electric and magnetic currents equivalent to those of the updated residual field recorded at the location of the receivers; and Constructing the updated volume images of anomalous conductivity $\tilde{\sigma}_{a(n)}(r)$ and of anomalous permittivity $\in_{a(n)}(r)$ on the basis of updated cross power spectrum or cross correlation functions between said background field and said updated backscattering field, using regularization procedures.

Embodiments of a Security Screening Device

Figure 8:
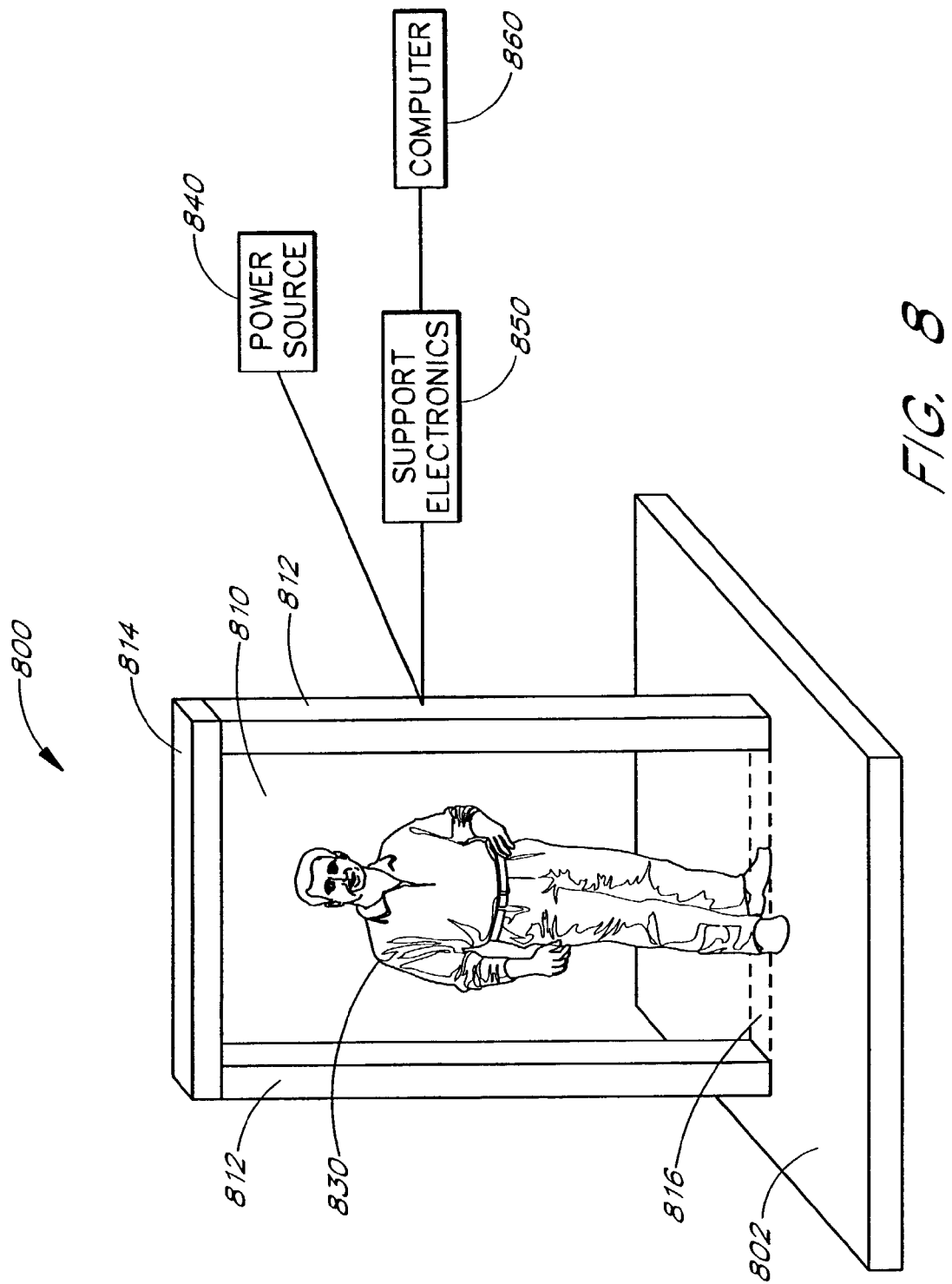
FIG. 8 is a schematic illustration of one embodiment of a security screening and inspection device.

FIG. 8 illustrates one embodiment of a security screening device 800. In such embodiments, the security screening device 800 comprises a portal 810 adapted to allow a person 830 to walk therethrough. In the embodiment illustrated in FIG. 8, the portal 810 comprises vertical support posts 812, a top portion 814, and a baseplate 816 that is integrated into the underlying floor 802. A power source 840 supplies power to the portal 810.

When a person 830 passes through the portal 810, one or more transmitters (not shown) placed within the vertical support posts 812, the top portion 814, and the baseplate 816 produce electromagnetic fields. At the same, time, one or more receivers (not shown) placed within the vertical support posts 812, the top portion 814, and the baseplate 816 record electromagnetic fields. The recorded analog signals are converted by a support electronics module 850 to digital signals. A computer 860 receives the digital signals of the scattered electromagnetic field from the support electronics module, creates a simulated homogeneous background field that represents the examined background medium without the examined target (such as the person's body and any objects attached to the person's body), creates a simulated backscattering anomalous field that represents an electromagnetic field obtainable by transmitting the scattered electromagnetic field from the receivers to illuminate the background medium, and produces a volume image of the conductivity and/or dielectric permittivity of the examined target (such as the person's body and any objects attached to the person's body).

As used herein, "objects attached to the person's body" refers to any item which may be fixably or non-fixably attached to the person's body, to clothing worn by the person, or to objects carried by the person. For example, a weapon placed in a pocket of a jacket worn by a person would be encompassed within the term "objects attached to the person's body."

In alternative embodiments, the computer 860 produces the volume image by calculating cross power spectra of the background field and the backscattering field. In yet another embodiment, the computer 860 produces the volume image by calculating cross correlation functions between the background field and the backscattering field. The operator may inspect any the images produced by the computer on a monitor in the same manner as is done with the X-ray images.

CONCLUSION

The application includes Appendix A titled "Method of Medical Broad Band Electromagnetic Holographic Imaging." The following articles are also incorporated by reference in their entirety: M. S. Zhdanov, S. Fang and G. Hursan, 2000, Electromagnetic inversion using quasi-linear approximation, Geophysics, 65, No. 5, 1501-1513; M. S. Zhdanov and G. Hursan, 2000, 3-D electromagnetic inversion based on quasi-analytical approximation, Inverse Problems, 16, 1297-1322.

The invention may be embodied in other specific forms without departing from the essential characteristics as described herein. The embodiments described above are to be considered in all respects as illustrative only and not restrictive in any manner. The scope of the invention is indicated by the following claims and their equivalents rather than by the foregoing description.

What is claimed is:

1. A system of security screening a body and attached object, comprising:
   a portal including at least one transmitter coil and at least one receiver coil, wherein said portal is configured to accommodate said body and attached object passing therethrough; wherein said transmitter coil is configured to generate a broadband electromagnetic field comprising a frequency domain electromagnetic field and/or time domain electromagnetic field that propagates through said body and attached object and interacts with said body and attached object to result in a scattered electromagnetic field; and wherein said receiver coil is configured to record said scattered electromagnetic field; and
   a computer configured to simulate a first background electromagnetic field existing within said portal when there is no body and attached object within said portal, to compute a first backscattering electromagnetic field obtainable by transmitting said scattered electromagnetic field from said receiver coil, to produce an image of electric conductivity and/or dielectric permittivity of said body and attached object, and to determine at least one characteristic of the attached object;
   wherein the computer is configured to produce the image by:
      calculating a second background electromagnetic field in response to said first background electromagnetic field;
      calculating a residual electromagnetic field between the second background electromagnetic field and the first backscattering electromagnetic field;
      calculating a second backscattering field for the residual electromagnetic field by simulating illumination of the updated background medium; and
      constructing updated volume images on the basis of updated cross power spectrum or cross correlation functions between said first background field and said second backscattering field.

2. The system of claim 1, wherein the attached object comprises a weapon.

3. The system of claim 1, wherein the determined characteristic of the attached object is material composition.

4. The system of claim 1, wherein the determined characteristic of the attached object is shape.

5. The system of claim 1, wherein said computer is configured to produce said image by calculating cross power spectra of said first background electromagnetic field and said first backscattering electromagnetic field.

6. The system of claim 1, wherein said computer is configured to produce said image by calculating cross correlation functions between said first background electromagnetic field and said first backscattering electromagnetic field.

7. The system of claim 1, further comprising one or more support posts connected to said portal and configured to support said portal.

8. The system of claim 7, wherein said one or more support posts are adjustable in height.

9. The system of claim 7, wherein said portal is adjustable in height along said one or more support posts.

10. The system of claim 1, further comprising a converter configured to receive analog signals of said scattered electromagnetic field from said receiver coils, to convert said received analog signals into digital signals of said scattered electromagnetic field, and to transmit said digital signals to said computer.

11. The system of claim 1, wherein said receiver coils are further configured to record said generated electromagnetic field, said system further comprising a filter configured to receive said generated electromagnetic filed and said scattered electromagnetic field from said receiver coils, to filter said generated electromagnetic field from said scattered electromagnetic field, and to transmit said scattered electromagnetic field to said computer.

12. A system of security screening a body and attached object, comprising:
  a portal including at least one transmitter coil and at least one receiver coil, wherein said portal is configured to accommodate said body and attached object passing therethrough; wherein said transmitter coil is configured to generate a broadband electromagnetic field comprising a frequency domain electromagnetic field and/or time domain electromagnetic field that propagates through said body and attached object and interacts with said body and attached object to result in a scattered electromagnetic field; and wherein said receiver coil is configured to record said scattered electromagnetic field;
  a computer configured to simulate a first background electromagnetic field existing within said portal when there is no body and attached object within said portal, to compute a first backscattering electromagnetic field obtainable by transmitting said scattered electromagnetic field from said receiver coil, to produce an image of electric conductivity and/or dielectric permittivity of said body and attached object, and to determine at least one characteristic of the attached object;
  wherein said computer is configured to produce said image iteratively by:
    calculating a second background electromagnetic field in response to said first background electromagnetic field with a previously obtained complex conductivity;
    calculating a residual electromagnetic field between the second background electromagnetic field and the first backscattering electromagnetic field;
    calculating a second backscattering field for the residual electromagnetic field by simulating illumination of the updated background medium with electric and magnetic currents equivalent to those of the updated residual electromagnetic field recorded at the location of the receivers; and
    constructing updated volume images of anomalous conductivity $\sigma_{a(n)}(r)$ and of anomalous permittivity $\in_{a(n)}(r)$ on the basis of updated cross power spectrum or cross correlation functions between said first background field and said second backscattering field, using regularization procedures.

13. The system of claim 12, wherein the attached object comprises a weapon.

14. The system of claim 12, wherein the determined characteristic of the attached object is material composition.

15. The system of claim 12, wherein the determined characteristic of the attached object is shape.

16. The system of claim 12, wherein said computer is configured to produce said image by calculating cross power spectra of said first background electromagnetic field and said first backscattering electromagnetic field.

17. The system of claim 12, wherein said computer is configured to produce said image by calculating cross correlation functions between said first background electromagnetic field and said first backscattering electromagnetic field.

18. The system of claim 12, further comprising one or more support posts connected to said portal and configured to support said portal.

19. The system of claim 18, wherein said one or more support posts are adjustable in height.

20. The system of claim 18, wherein said portal is adjustable in height along said one or more support posts.

21. The system of claim 12, further comprising a converter configured to receive analog signals of said scattered electromagnetic field from said receiver coils, to convert said received analog signals into digital signals of said scattered electromagnetic field, and to transmit said digital signals to said computer.

22. The system of claim 12, wherein said receiver coils are further configured to record said generated electromagnetic field, said system further comprising a filter configured to receive said generated electromagnetic filed and said scattered electromagnetic field from said receiver coils, to filter said generated electromagnetic field from said scattered electromagnetic field, and to transmit said scattered electromagnetic field to said computer.

23. A method of security screening a body and attached object, comprising:
  providing a portal adapted to passably receive said body and attached object, wherein said portal includes at least one transmitter coil and at least one receiver coil, wherein said transmitter coil is adapted to generate a broadband electromagnetic field comprising a frequency domain electromagnetic field and/or a time domain electromagnetic field that propagates through said body and attached object and that interacts with said body and attached object to result in a scattered electromagnetic field, and wherein said receiver coil is adapted to record said scattered electromagnetic field;
  simulating a first background electromagnetic field existing within said portal when there is no body and attached object within said portal;
  computing a first backscattering electromagnetic field obtainable by transmitting the scattered electromagnetic field from said receiver coil;
  producing an image of electric conductivity and/or dielectric permittivity of said body and attached object;
  calculating a second background electromagnetic field in response to said first background electromagnetic field;
  calculating a residual electromagnetic field between the second background electromagnetic field and the first backscattering electromagnetic field;
  calculating a second backscattering field for the residual electromagnetic field by simulating illumination of the updated background medium; and
  constructing updated volume images on the basis of updated cross power spectrum or cross correlation functions between said first background field and said second backscattering field; and
  determining at least one characteristic of said attached object.

24. The method of claim 23, wherein the attached object is a weapon.

25. The method of claim 23, wherein the determined characteristic of the attached object is material composition.

26. The method of claim 23, wherein the determined characteristic of the attached object is shape.

27. The method of claim 23, wherein the step of producing said image further comprises calculating cross power spectral of said first background electromagnetic field and said first backscattering electromagnetic field.

28. The method of claim 23, wherein the step of producing said image further comprises calculating cross correlation functions between said first background electromagnetic field and said first backscattering electromagnetic field.

29. The method of claim 23, further comprising connecting one or more support posts to said portal, wherein said support posts are configured to support said portal.

30. The method of claim 29, wherein said one or more support posts are adjustable in height.

31. The method of claim 29, wherein said portal is adjustable in height along said one or more support posts.

32. The method of claim 23, further comprising:
receiving analog signals of said scattered electromagnetic field from said receiver coils; and
converting said received analog signals into digital signals of said scattered electromagnetic field.

33. The method of claim 23, further comprising:
recording said generated electromagnetic field with said received coils; and
filtering said generated electromagnetic field from said scattered electromagnetic field.

34. A method of security screening a body and attached object, comprising:
providing a portal adapted to passably receive said body and attached object, wherein said portal includes at least one transmitter coil and at least one receiver coil, wherein said transmitter coil is adapted to generate a broadband electromagnetic field comprising a frequency domain electromagnetic field and/or a time domain electromagnetic field that propagates through said body and attached object and that interacts with said body and attached object to result in a scattered electromagnetic field, and wherein said receiver coil is adapted to record said scattered electromagnetic field;
simulating a first background electromagnetic field existing within said portal when there is no body and attached object within said portal;
computing a first backscattering electromagnetic field obtainable by transmitting the scattered electromagnetic field from said receiver coil;
producing an image of electric conductivity and/or dielectric permittivity of said body and attached object;
determining at least one characteristic of said attached object;
calculating a second background electromagnetic field in response to said first background electromagnetic field with a previously obtained complex conductivity;
calculating a residual electromagnetic field between the second background electromagnetic field and the first backscattering electromagnetic field;
calculating a second backscattering field for the residual electromagnetic field by simulating illumination of the updated background medium with electric and magnetic currents equivalent to those of the updated residual electromagnetic field recorded at the location of the receivers; and
constructing updated volume images of anomalous conductivity $\sigma_{a(n)}(r)$ and of anomalous permittivity $\in_{a(n)}(r)$ on the basis of updated cross power spectrum or cross correlation functions between said first background field and said second backscattering field, using regularization procedures.

35. The method of claim 34, wherein the attached object is a weapon.

36. The method of claim 34, wherein the determined characteristic of the attached object is material composition.

37. The method of claim 20, wherein the determined characteristic of the attached object is shape.

38. The method of claim 20, wherein the step of producing said image further comprises calculating cross power spectral of said first background electromagnetic field and said first backscattering electromagnetic field.

39. The method of claim 20, wherein the step of producing said image further comprises calculating cross correlation functions between said first background electromagnetic field and said first backscattering electromagnetic field.

40. The method of claim 20, further comprising connecting one or more support posts to said portal, wherein said support posts are configured to support said portal.

41. The method of claim 40, wherein said one or more support posts are adjustable in height.

42. The method of claim 40, wherein said portal is adjustable in height along said one or more support posts.

43. The method of claim 20, further comprising:
receiving analog signals of said scattered electromagnetic field from said receiver coils; and
converting said received analog signals into digital signals of said scattered electromagnetic field.

44. The method of claim 20, further comprising:
recording said generated electromagnetic field with said received coils; and
filtering said generated electromagnetic field from said scattered electromagnetic field.

* * * * *